United States Patent [19]
Berg et al.

[11] Patent Number: 6,061,140
[45] Date of Patent: May 9, 2000

[54] SPECTROPHOTOMETER WITH SELECTABLE MEASUREMENT AREA

[75] Inventors: Bernard J. Berg, Kentwood; Marc D. Zuiderveen, Hudsonville; Thomas J. Boes, Grandville, all of Mich.

[73] Assignee: X-Rite, Incorporated, Grandville, Mich.

[21] Appl. No.: 09/320,779

[22] Filed: May 27, 1999

[51] Int. Cl.$^7$ .............................. G01J 3/51; G01N 21/27
[52] U.S. Cl. ....................... 356/418; 356/236; 250/226; 250/228
[58] Field of Search ..................................... 356/319, 326, 356/328, 236, 402, 405, 406, 407, 416, 418, 419, 445, 446; 250/226, 228

[56] References Cited

U.S. PATENT DOCUMENTS 5,369,481  11/1994  Berg et al. .............................. 356/236

OTHER PUBLICATIONS

U.S. Pat. application No. 08/305,870, filed Sep. 14, 1994, by Bernard J. Berg et al and Entitled "Compact Spectrophotometer".

U.S. Pat. application No. 08/368,208, filed Dec. 30, 1994, by Bernard J. Berg et al and Entitled "Compact Spectrophotometer".

U.S. Pat. application No. 08/714,969, filed Sep. 17, 1996, by Bernard J. Berg et al and Entitled "Compact Spectrophotometer".

P.A. Palumbo et al, Novel spectrophotometer for the measurement of color and appearance, 380 Analytica Chimica Acta pp. 243–261 (1999).

*Primary Examiner*—F. L. Evans
*Attorney, Agent, or Firm*—Warner Norcross & Judd

[57] ABSTRACT

A spectrophotometer providing a sample measurement area of selectable size. The spectrophotometer includes a sphere defining a sample station, a lamp to illuminate the interior of the sphere and therefore the sample station, a color measurement engine including an aperture directed toward the sample station, and a measurement area size selector. The size selector includes a movable plate defining two or more holes of different sizes. The plate can be moved so that only one of the holes is aligned with the aperture to control the size of the measurement area sampled by the color measurement engine.

12 Claims, 7 Drawing Sheets

SPECTROPHOTOMETER WITH SELECTABLE MEASUREMENT AREA

BACKGROUND OF THE INVENTION

The present invention relates to spectrophotometers, and more particularly to spectrophotometers having selectable measurement areas.

Spectrophotometers are instruments used to determine the color of an object. A spectrophotometer typically includes a source of illumination to illuminate the object, a color measurement engine for detecting light reflected from the sample; and signal processing circuitry connected to the light measurement engine to compute curves or numerical values indicative of color. The general principles of construction and use of spectrophotometers are well known to those skilled in the art.

One type of spectrophotometer uses an integrating sphere in which the light illuminating the sample is integrated to provide diffuse, uniform illumination over an exposed measurement area of the sample. An example of such a spectrophotometer is illustrated in U.S. Pat. No. 5,369,481, issued Nov. 29, 1994 to Berg et al and entitled "Portable Spectrophotometer." This device provides a measurement area that is a circle of fixed diameter. Unfortunately, in order to sample measurement areas of different sizes, multiple devices designed for different measurement areas must be used. Alternatively, portions of the optics or the color measurement engine of a single device can be manually interchanged to accommodate different measurement areas, but this requires undesirably complicated user procedures.

SUMMARY OF THE INVENTION

The aforementioned problem is overcome in the present invention wherein the sample measurement area of a spectrophotometer is selectable from a variety of different sizes or characteristics. More particularly, the spectrophotometer includes a sample station, a source of illumination, a color measurement engine, and a measurement area size selector. The sample measurement size is selected by physically defining the area of reflected light presented to the color measurement engine. This is done, for example, using apertures of different sizes, or an iris, between the sample and the color measurement engine.

As specifically disclosed, the measurement area size selector is a plate defining the apertures of different sizes. The plate is moveable to align one of the plate apertures on a line between the sample area and the color measurement engine. The size of the measurement area is selected by selecting the size aperture to be aligned with the optics.

The present invention provides an effective, efficient, relatively low-cost mechanism for selecting and controlling the size of the sample measurement area.

These and other objects, advantages, and features of the invention will be more readily understood and appreciated by reference to the detailed description of the preferred embodiment and the drawings.

DETAILED DESCRIPTION OF THE PREFERRED EMBODIMENT

Figure 1:
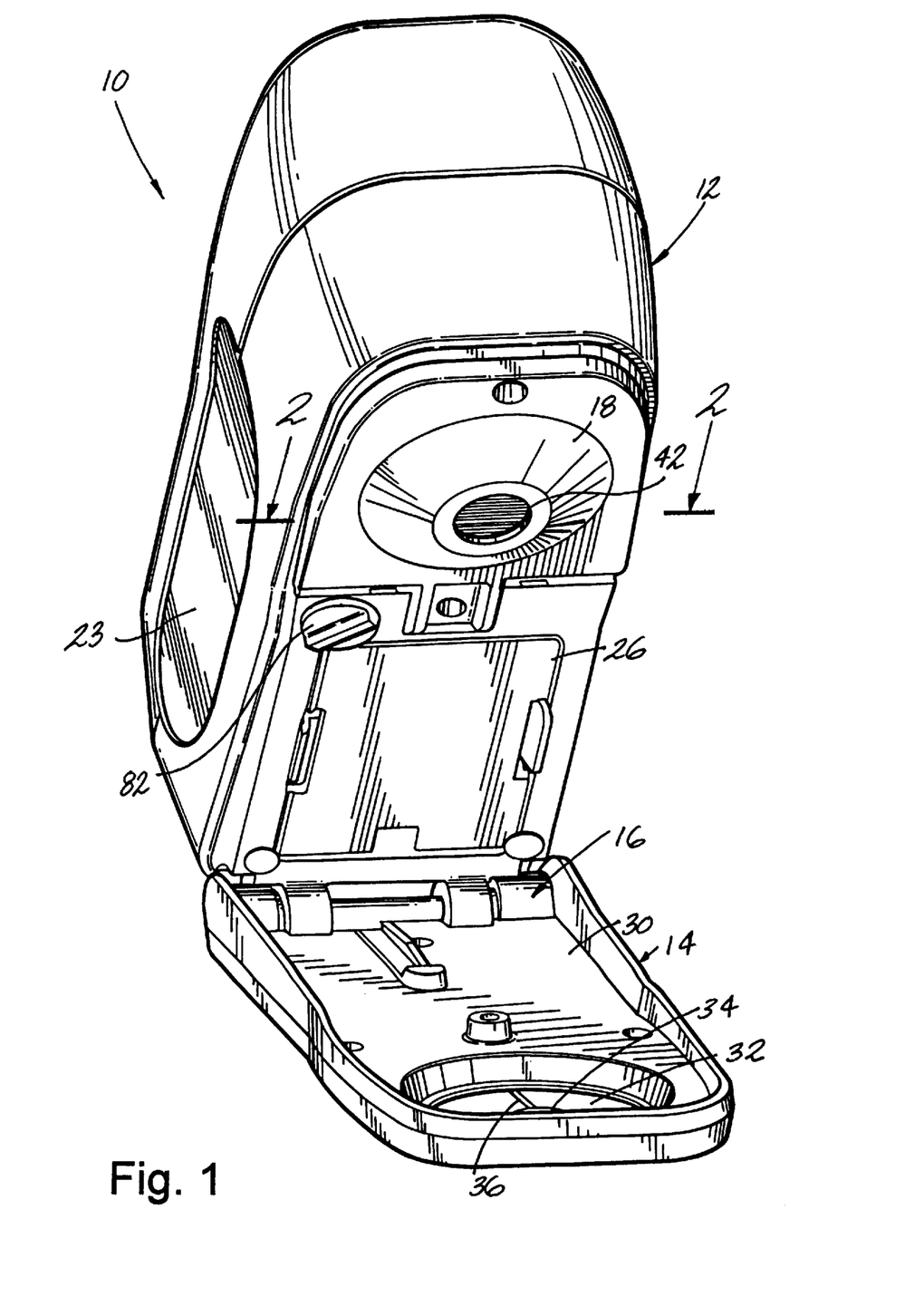
FIG. 1 is a perspective view of the spectrophotometer of the present invention.

A spectrophotometer constructed in accordance with a preferred aspect of the invention is illustrated in the drawings and generally designated 10. As seen in FIG. 1, the spectrophotometer generally includes a housing 12, and a foot 14 hingedly interconnected at a hinge 16. As seen in FIGS. 2–5, a sphere 18 and a color measurement engine 20 are supported within the housing 12. An aperture plate 22 is slidably mounted within the color measurement engine 20. The aperture plate 22 includes small apertures 24 and large apertures 26. The apertures are arranged in pairs of one each. Both sets of apertures are visible in FIG. 3. Only one set of the apertures is visible in FIGS. 4 and 5 because a portion of the aperture plate 22 has been cut away above the SPIN aperture. The position of the plate 22 is manually selected to determine the size of the measurement area presented to the light measurement engine 20. Consequently, the size of the measurement area is easily, efficiently, and economically controlled.

I. Housing and Shoe

The physical configuration of the housing 12 and the shoe 14 (FIG. 1) are conventional to those skilled in the art. The unit 10 is "hand-held" or "portable." The housing 12 can easily be grasped by a single human hand using the rubber over-molded side grips 23 (only one visible) on opposite sides of the unit 10. A removable battery pack 26 is received within a battery compartment (not visible). The power options and configurations are well known to those skilled in the art.

The shoe 14 is also of generally conventional design and provides a "foot" for the unit 10. The unit 14 includes a generally flat body 30 and a target window 32 releasably mounted therein. The target window 32 defines a central circular opening 34 and crosshairs 36 aligned with the opening. The opening 34 defines an area slightly larger than the measurement area and facilitates alignment of the unit 10 with the area to be sampled. Preferably, one target window 32 is included with the unit 10 for each of the selectable measurement sizes. This feature of the shoe 14 is not conventional. Each of the included windows 32 defines an opening 24 unique in size, shape, or other characteristic corresponding to the associated measurement area characteristic. One of the target windows 32 is retained within the body 30 for example by way of a snap-fit so that the windows 32 are easily, manually removable and insertable.

The hinge 16 interconnecting the housing 12 and the shoe 14 is also generally well known. The hinge 16 is spring-loaded so that shoe 14 is pushed to the position illustrated in FIG. 1 when the housing 12 is held in one's hand. When a measurement is to be taken, the operator pushes the housing 12 against the foot 14, again as is known in the art. As is conventional, the shoe is "flippable" meaning that it can be unlocked and rotated about the hinge 16 away from the area directly below the housing 12.

II. Integrating Sphere and Illuminator

The integrating sphere 18 (FIGS. 2–5) is of generally conventional construction. As disclosed, the sphere has an internal diameter of 2.5 inches and is fabricated of a material sold by LabSphere Inc. under the trademark SPECTRALON. The sphere includes an upper half 38 and a lower half 39 which together define a spherical interior 40. The lower half 39 defines a sample port 42, which is circular and larger than any of the selectable measurement areas. The sample port 42 defines a sample station.

Figure 2:
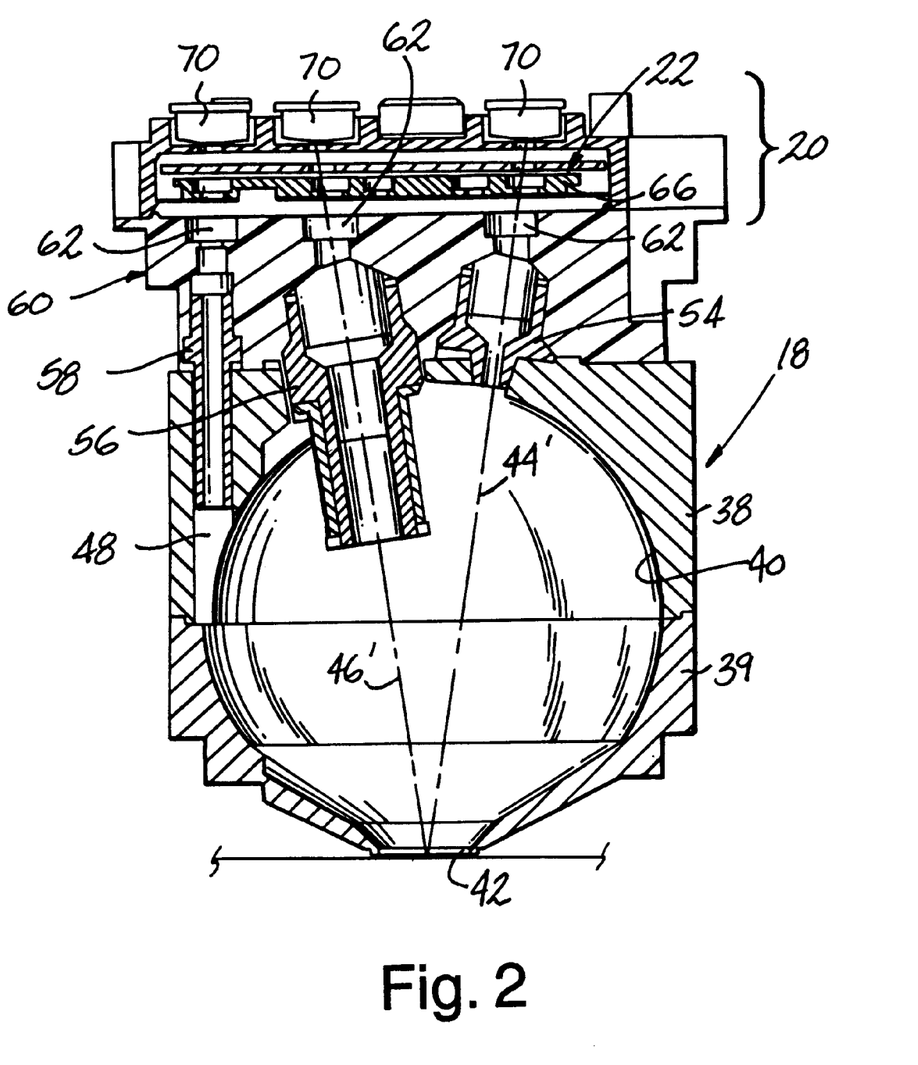
FIG. 2 is a sectional view (with the housing removed) taken along line II—II in FIG. 1.
Figure 3:
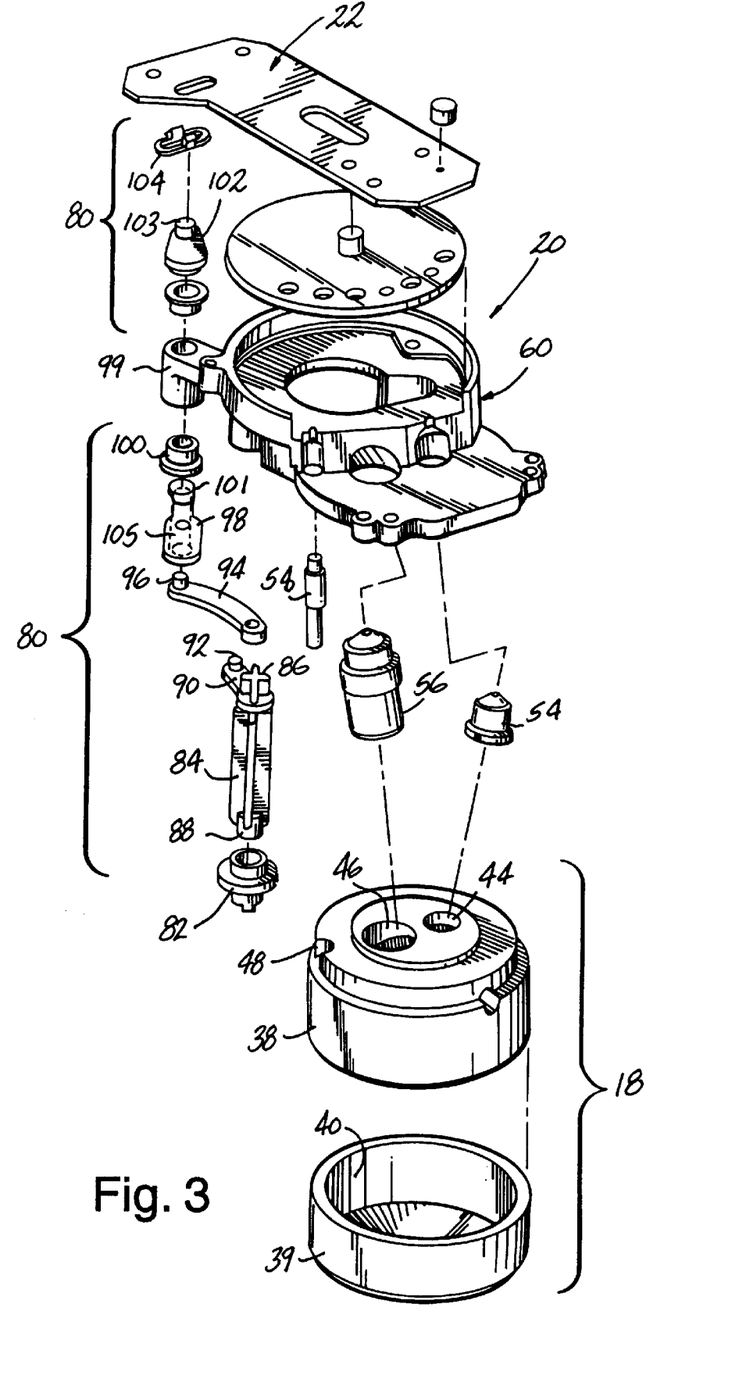
FIG. 3 is a perspective exploded view of the integrating sphere, the color measurement engine, and the sample size selector mechanism.
Figure 4:
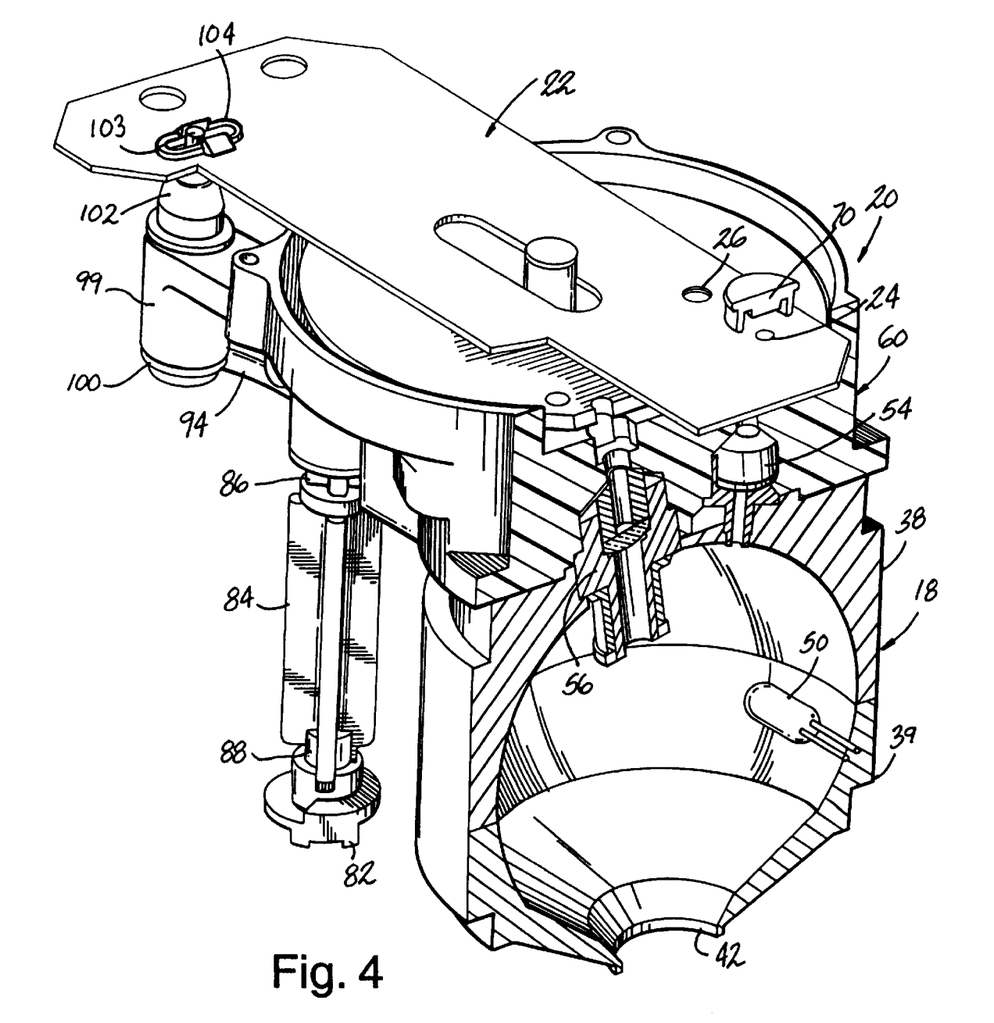
FIG. 4 is a perspective sectional view of the assembled components illustrated in FIG. 3 showing the aperture plate in the "small" position.
Figure 5:
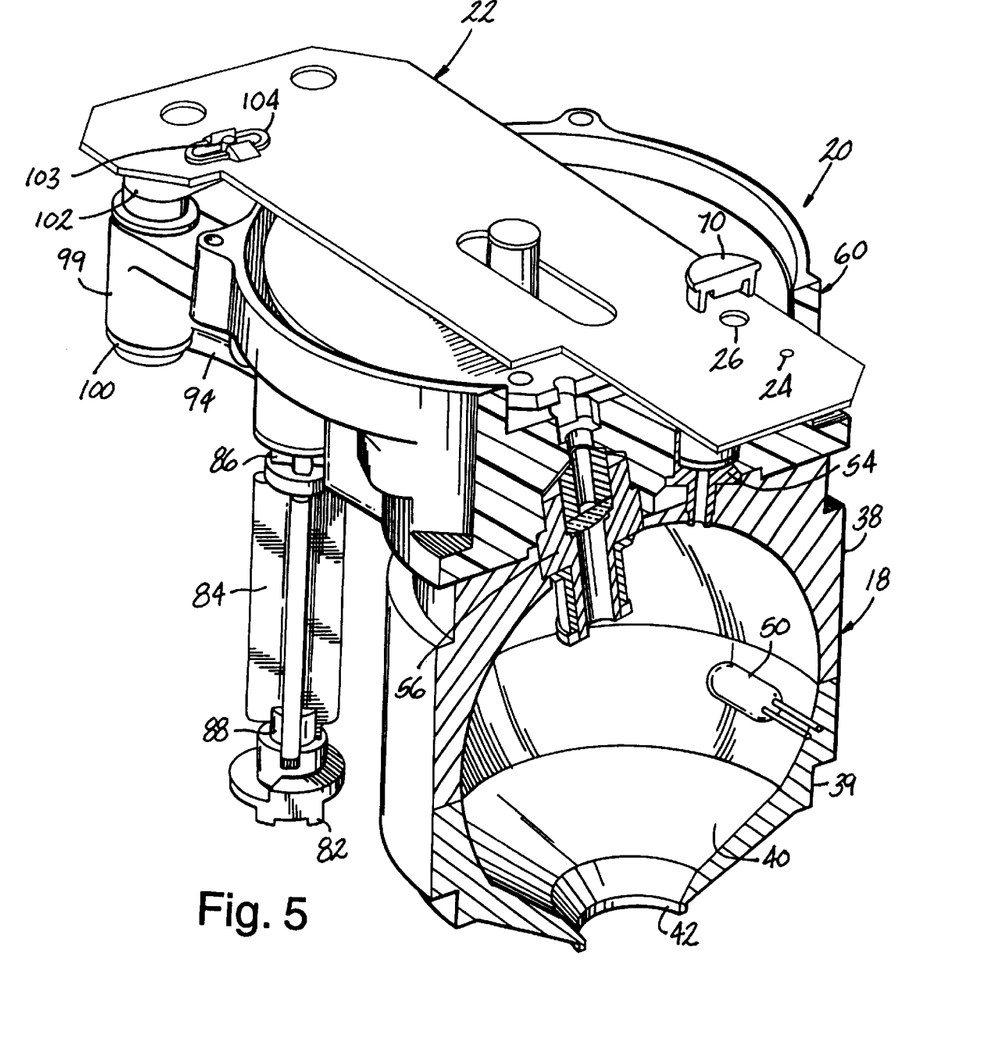
FIG. 5 is a view similar to FIG. 4 but showing the aperture plate in the "large" position.
Figure 6:
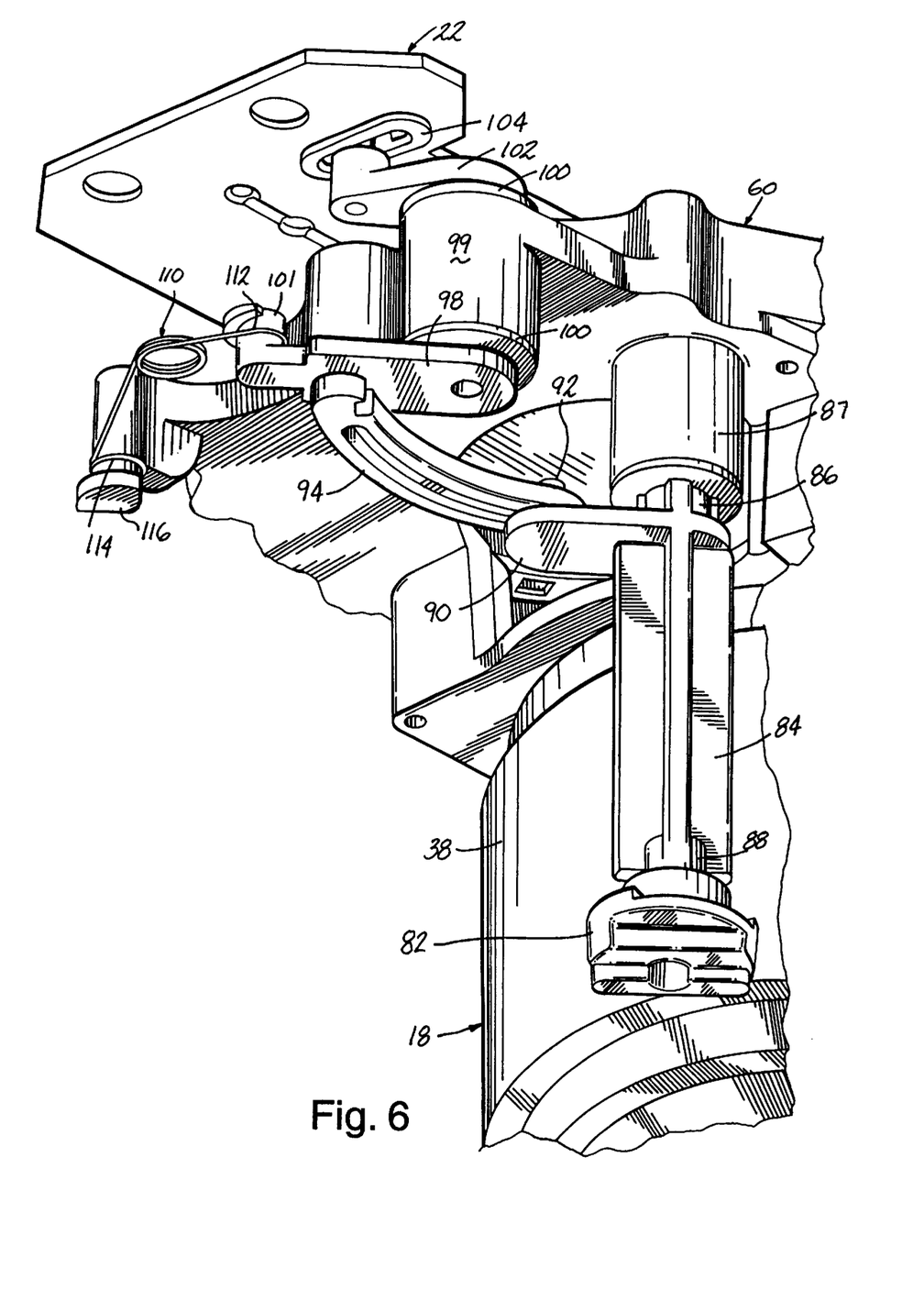
FIG. 6 is a bottom perspective view of the linkage of the sample size selector mechanism.
Figure 7:
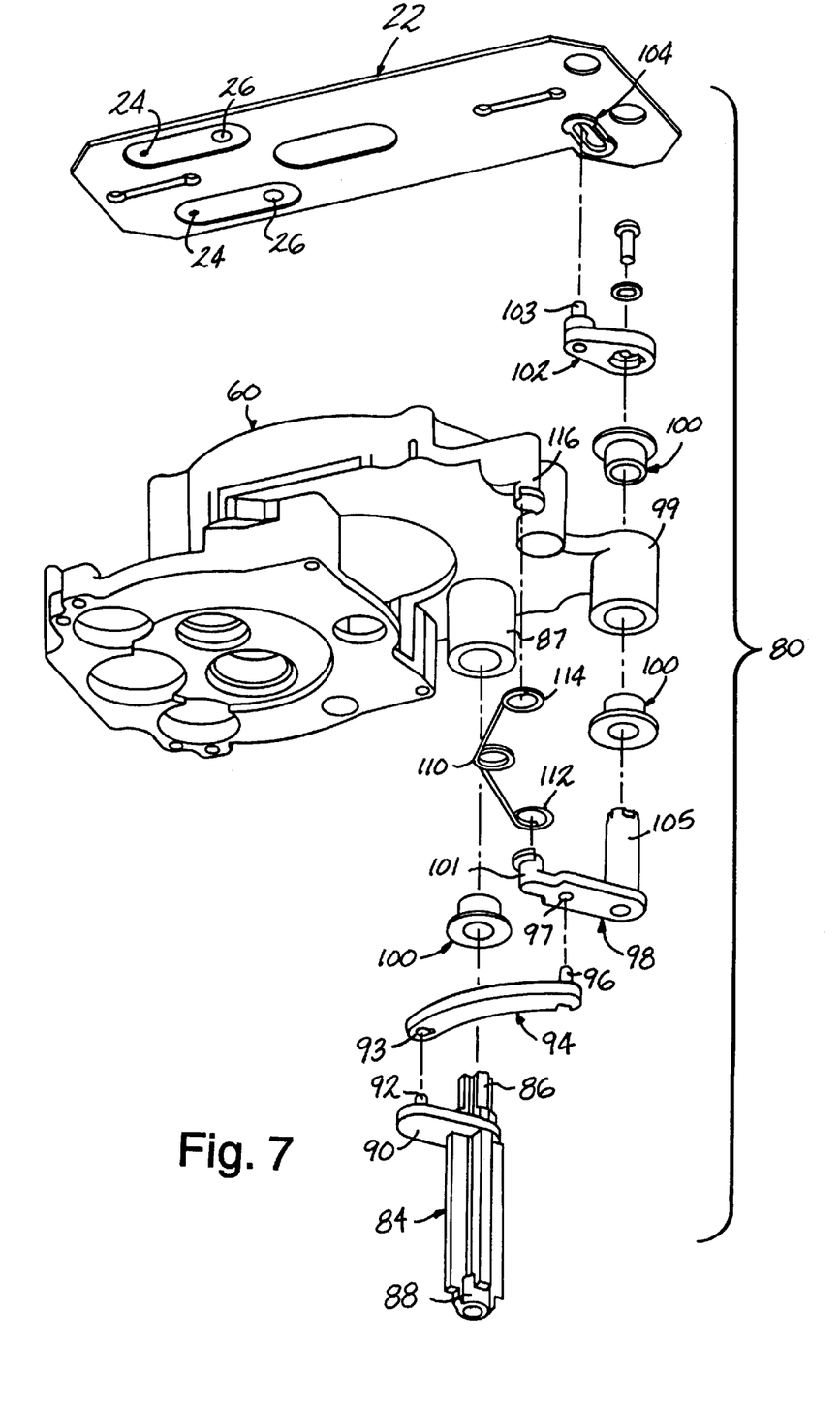
FIG. 7 is a bottom perspective exploded view of the linkage of the sample size selector mechanism taken from a different angle than FIG. 6.

As perhaps best illustrated in FIG. 3, the integrating sphere 18 and more particularly the upper half 38 defines a SPEX port 44, a SPIN port 46, and a WALL port 48. The ports 44, 46, and 48 are all cylindrical. The axes 44' and 46' (FIG. 2) are aligned with the center of the sample port 42. Each axis 44' and 46' is offset 8° from normal to produce the standard d/8 geometry as is customary in the art. The wall aperture 48 is generally tangent to the interior 40 of the sphere 18.

A gas pressure tungsten lamp 50 (FIGS. 4 and 5) is included within the sphere 18 as a source of illumination or illumination means. Suitable lamps are known to those skilled in the art. Additionally, a baffle or similar structure (not shown) is included to prevent direct illumination of the sample port 42 by the lamp 50.

III. Apertures

The construction of the integrating sphere and apertures are generally well known to those skilled in the art. For example, these components are illustrated and described in U.S. Pat. No. 5,369,481 issued Nov. 29, 1994 to Berg et al, the disclosure of which is hereby incorporated by reference. Accordingly, a detailed description of these components need not be repeated.

The SPEX and SPIN apertures are opposite one another about a line normal to the sample port 42. The SPEX aperture 54 is mounted within the SPEX port 44 (FIGS. 2 and 3). The SPEX aperture measures the diffuse component and a small amount of the specular component. The reflectance from the relatively large black area of the SPIN aperture and the reflectance from the sphere around the SPIN aperture result in only a small amount of specular light striking the sample and reflecting into the SPEX aperture.

The SPIN aperture 56 is mounted within the SPIN port 46. The SPIN aperture measures the diffuse component and most of the specular component. The relatively small aperture hole and black area of the SPEX aperture prevent only a small portion of the specular component from striking the sample and reflecting into the SPIN aperture.

The information acquired from the SPIN and SPEX apertures 54 and 56 is used to calculate the "SPecular INcluded reflectance" (also known as the "total reflectance") and the "SPecular EXcluded reflectance" (also known as the "diffuse reflectance"). The specular included reflectance includes both the diffuse and specular components. The specular excluded reflectance includes only the diffuse component; the specular component is completely excluded.

The WALL aperture 58 is mounted within the WALL port 48. The WALL aperture views the sphere wall. The signal measured in this aperture allows correction for changes in illumination relative to calibration levels.

The SPIN and SPEX apertures collect light reflected from the diffusely illuminated sample, and the WALL aperture collects light reflected from the sphere wall. Each of the three apertures is basically an aperturing column which limits the area from which light is collected.

IV. Color Measurement Engine

The general construction and operation of the color measurement engine is illustrated and described in co-pending Application No. 08/714,969, filed Sep. 17, 1996 by Berg et al, now U.S. Pat. No. 6,002,488, which is a continuation of Application No. 08/305,870, filed Sep. 14, 1994 by Berg et al (now abandoned), which is a continuation-in-part of Application No. 08/368,208, filed Dec. 30, 1994 by Berg et al (now abandoned). The disclosures of all three applications are incorporated by reference.

The color measurement engine 20 includes a body 60 supporting the remaining components and receiving the upper ends of each of the apertures 54, 56, and 58. (See FIGS. 2–5.) Three static ultraviolet/infrared (UV/IR) blocking filters 62 are located above and are optically aligned with each of the apertures 54, 56, and 58. The blocking filters 62 pass light in the visible spectrum (i.e. in the range of 400 nanometers (nm) to 700 nm) so that the photodiodes 70 are not undesirably affected by wavelengths outside of the visible spectrum. The blocking filters 62 are well known to those skilled in the art.

The color measurement engine 20 further includes a rotatable filter wheel 66 supporting a plurality of dynamic interference filters in a circular configuration around the perimeter of the wheel. In the preferred embodiment, 31 filters are included and each has unique spectral properties to filter a unique portion of the spectrum of reflected light. The 31 filters cover the spectral range of 400 nanometers (nm) to 700 nm in 10 nm increments. Each of the filters is a narrow passband filter (e.g. a half-power bandwidth of 15 nm), and the filters are rotated sequentially past each of the apertures 54, 56, and 58 as the filter wheel rotates. The apertures 54, 56, and 58 are aligned with the radial arc of the filters within the filter wheel.

Finally, the color measurement engine 20 includes three photodiodes 70, each aligned with one of the apertures 54, 56, and 58. The photodiodes convert the light energy passing through the respective aperture, static filter, and dynamic filter into a voltage proportional to the received light intensity. The apertures 54, 56, and 58 are sampled through each of the 31 filters during every two revolutions of the filter wheel. That is to say that not every filter is sampled during a single revolution of the wheel. The filter wheel is rotated at a speed of 12 revolutions per second (rps), and 8 samplings of each of the 31 filters is averaged to produce each of the 31 readings.

V. Measurement Area Selector

The measurement areas selector includes the aperture plate 22 and the actuating mechanism or linkage 80. (See FIGS. 3–7.) The only visible component of the actuator mechanism in the assembled unit 10 is the knob 82 (see FIG. 1). The knob may be grasped by a user and rotated through an angle of approximately 100 degrees to shift the aperture plate 22 between its first and second, or "small" and "large" opposite positions.

The aperture plate 22 defines a three small aperture 24 and three large apertures 26. Each of the apertures 24 and 26 are generally circular. The diameter of the small aperture 24 above the SPEX aperture 54 is 0.044 inch, and the diameter of the small aperture above the SPIN aperture 56 is 0.061 inch. The diameter of the large aperture 26 above the SPEX aperture 54 is 0.109 inch. The large aperture 26 is slightly oblong—being somewhat more narrow in the circumferential direction than in the radial direction—to reduce the likelihood of overlap between samplings of adjacent filter wheel windows. Specifically, the major (radial) axis is 0.143 inch, and the minor (circumferential) axis is 0.110 inch. The size, shape, and other characteristics of the apertures 24 and 26 can be selected depending on the desired measurement characteristics.

The knob 82 is fixedly connected to an extension rod 84, which is pivotally supported at its upper end 86 within a socket 87 integral with the housing 60 and at its lower end 88 within the housing 12. The extension rod 84 includes a radially extending finger 90 having a pin 92 pivotally fitted within a socket 93 in a bell crank 94, which in turn includes a pin 96 pivotally fitted within a socket 97 in a crank 98. A post 105 on the crank 98 is pivotally supported within a socket 99 integral with the housing 60. Bushings 100 are included between the housing sockets 87 and 99 and the pivotally supported pieces of the linkage 80. A crank 102 is fixedly secured to the upper end of the post 105, which extends fully through the socket 99. The crank 102 includes a pin 103. An elongated bushing 104 is secured within the aperture plate 22 and receives the pin 103 of the crank 102.

An over-center spring 110 (FIGS. 6 and 7 only) is included to ensure that the linkage 80, and therefore the aperture plate 22, travels to one of its two extreme positions. This ensures that either small apertures 24 or large apertures 26 are properly registered with the measurement engine 20. The over-center spring 110 includes a first terminal loop 112 mounted about the spring lug 101 of the crank 98 and a second terminal loop 114 mounted about a spring lug 116 on the housing 60. Other suitable over-center springs or other mechanisms can be used and will readily recognized by those skilled in the art.

Rotation of the knob 82 is translated through the linkage to rotate the crank 102 through an angle of approximately 100 degrees. The rotation of the crank 102 results in movement of the aperture plate 22 between first and second, or forward an rearward, or "small" and "large" positions. A detent structure (not shown) retains the plate 22 in either of the selected position. The small holes 24 are optically aligned with the apertures 54, 56, and 58 when the plate 22 is in the first, forward, or small position; and the large holes 26 are optically aligned with the apertures with the plate is in the second, rearward, or large position.

Circuitry (not illustrated) is operatively connected to the color measurement engine to sample the signal strength through each of the apertures 54, 56, and 58 as each of the 31 filters within the filter wheel are aligned with the apertures. The circuitry is controlled by a computer program to produce spectral data and information from the sample data. Access ports at the rear of the housing 12 (not visible) allow RS232 communication, power from an AC adapter, and an on/off/reset switch. Particularly based on the disclosure of Application No. 08/714,969, now U.S. Pat. No. 6,002,488, the implementation of such control and measurement circuitry is known to those skilled in the art.

The selection of the position of the aperture plate 22 controls the effective size of the measurement area presented to the photodiodes 70. When the small apertures 24 are selected, the effective target sample size is approximately 4 millimeters (mm) in diameter. When the large apertures 26 are selected, the target sample size is approximately 8 millimeters in diameter.

As will be appreciated from the foregoing description, the effective size of the target area is selected efficiently, effectively, and economically by a characteristic of the physical apertures. In the disclosed embodiment, the characteristic is size. Other characteristics, such as shape, can also be appropriately selected by modifications to the apertures within the plate 22.

To assist the user in properly aligning the foot 14 (FIG. 1) with the area to be sampled, a target window 32 specific to the sample size preferably is installed. The appropriate target window 32 will include an aperture 34 slightly larger than the target area to be sampled. The correct window assists in physically identifying to the user the target area that will be sampled by the unit 10. The crosshairs 36 within the window 32 further assist in the alignment of the foot with the target area to be measured.

A high-contrast, 128×64-pixel graphics display is located on the top surface (not visible) of the housing 12 to provide a versatile means of communicating information to the user and of displaying the measured data. For example, the display confirms to the user when the sample-size has been changed via movement of the aperture plate 22. A 6-key user interface (not illustrated) is included on the top surface (not visible) of the housing 12 to provide a simple means of operating the instrument. Appropriate interfaces are generally known to those skilled in the art and need not be described in detail.

The disclosed embodiment provides a capability of selecting two measurement areas of different characteristics. It will be readily appreciated by those skilled in the art that the invention is readily extendable to provide a capability of selecting any other plurality of measurement areas of different characteristics.

Any reference to claim elements in the singular, for example, using the articles "a," "an," "the" or "said," is not to be construed as limiting the element to the singular.

The above description is that of a preferred embodiment of the invention. Various alterations and changes can be made without departing from the spirit and broader aspects of the invention as defined in the claims, which are to be interpreted in accordance with the principles of patent law including the doctrine of equivalents.

The embodiments of the invention in which an exclusive property or privilege is claimed are defined as follows:

1. A color measurement device comprising:

a sample station;

a source of illumination to illuminate said sample station and an object sample at said sample station;

a color measurement engine to measure light reflected from the sample, said engine including first and second ports, said sample area and said first port defining a first light path, said sample area and said second port defining a second light path, said engine further including first and second light detectors aligned with the first and second light paths respectively, said engine further including a rotatable filter wheel supporting a plurality of filters in a circular configuration, said wheel being positioned and said filters being spaced so that one of said filters is aligned with the first light path when another of said filters is aligned with the second light path, said engine further including a drive for automatically rotating said filter wheel to align said filters with said first and second ports in a desired sequence; and a measurement area size selector mechanism associated with said light measurement engine to select a size of a measurement area of said sample station, said selector mechanism defining a pair of small apertures and a pair of large apertures, said selector mechanism being movable so that either said pair of small apertures or said pair of large apertures are aligned with said first and second ports.

2. A color measurement device as defined in claim 1 wherein said size selector mechanism includes a plate defining said small and large apertures.

3. A color measurement device as defined in claim 2 wherein said plate is movable to align either said small apertures or said large apertures with said ports.

4. A color measurement device as defined in claim 3 wherein said plate is between said ports and said light detectors.

5. A color measurement device as defined in claim 1 wherein said apertures are circular.

6. A color measurement device as defined in claim 1 wherein said sample station includes a readily removable target window including indicator means for identifying the measurement area.

7. A color measurement device as defined in claim 1 wherein said size selector mechanism includes a hand-actuated knob.

8. A spectrophotometer comprising:

a sphere defining an interior, a sample port, and first and second measurement ports, said sample port and said first measurement port defining a first light path, said sample port and said second measurement port defining a second light path;

an illumination source to illuminate said interior of said sphere and said sample port;

a color measurement engine to measure light reflected from said sample port, said engine including first and second light detectors aligned with the first and second light paths respectively, said engine further including a rotatable filter wheel supporting a plurality of filters of different optical characteristics in a circular configuration aligned with the first and second light paths, said engine further including means for automatically rotating said filter wheel to repetitively align said filters with the light paths; and a measurement area size selector to select a size of a measurement area within said sample port to be measured by said measurement engine, said size selector including a body defining a pair of small apertures of equal size and a pair of large apertures of equal size, said large apertures being larger than said small apertures, said body being movable between a small position wherein each of said small apertures is aligned with one of the first and second light paths and a large position wherein each of said large apertures is aligned with one of the first and second light paths.

9. A spectrophotometer as defined in claim 8 wherein:

said first measurement port is a specular included port; and said second measurement port is a specular excluded port.

10. A spectrophotometer as defined in claim 8 wherein said apertures are circular.

11. A spectrophotometer as defined in claim 8 wherein said size selector includes:

a manually actuated knob; and a linkage interconnecting said knob and said body, whereby actuation of said knob results in movement of said body.

12. A spectrophotometer as defined in claim 8 wherein said sample port includes a manually removable target window having an alignment means for identifying the measurement area.

* * * * *